(12) United States Patent
Higuchi et al.

(10) Patent No.: US 6,896,704 B1
(45) Date of Patent: May 24, 2005

(54) MOVABLE FINGER FOR PROSTHESES, UPPER EXTREMITY PROSTHESES USING THIS MOVABLE FINGER, AND MOVABLE FINGER CONTROLLER

(75) Inventors: Tetsuya Higuchi, Tsukuba (JP); Masahide Harada, Sapporo (JP)

(73) Assignees: Harada Electronics Co., Ltd., Hokkaido (JP); National Institute of Advanced Industrial Science and Technology, Tokyo (JP); Tetsuya Higuchi C/O National Institute of Advanced Industrial Science and Technology, Ibaraki (JP)

( * ) Notice: Subject to any disclaimer, the term of this patent is extended or adjusted under 35 U.S.C. 154(b) by 0 days.

(21) Appl. No.: 09/979,033

(22) PCT Filed: May 19, 2000

(86) PCT No.: PCT/JP00/03219

§ 371 (c)(1),
(2), (4) Date: Jun. 5, 2002

(87) PCT Pub. No.: WO00/71060

PCT Pub. Date: Nov. 30, 2000

(30) Foreign Application Priority Data

May 19, 1999 (JP) .................................. 11-139150

(51) Int. Cl.[7] .............................. A61F 2/54; A61F 2/72
(52) U.S. Cl. .......................................... 623/64; 623/25
(58) Field of Search .......................... 623/25, 63, 64; 901/39; 294/111

(56) References Cited

U.S. PATENT DOCUMENTS

| 4,986,723 A | 1/1991 | Maeda |
| 5,336,269 A * | 8/1994 | Smits .......................... 623/25 |
| 5,413,611 A | 5/1995 | Haslam, II et al. |

FOREIGN PATENT DOCUMENTS

| EP | 0 421 780 A2 * | 4/1991 |
| FR | 923480 * | 7/1947 |

(Continued)

OTHER PUBLICATIONS

Hashimoto et al., "An Unilateral Master-Slave Hand System with a Force-controlled Slave Hand", IEEE International Conference, XP000657286, pp. 956-961, 1995.

Primary Examiner—David H. Willse
(74) Attorney, Agent, or Firm—Oliff & Berridge PLC

(57) ABSTRACT

A movable finger for prostheses, having a base a first intermediate portion connected to the base, a second intermediate portion connected to the first intermediate portion, and a fingertip connected to the second intermediate portion. The prosthesis further includes a first intermediate portion bending mechanism for actuating an actuator disposed in the base to pull a first wire to turn an eccentric member, a second intermediate portion bending mechanism for pulling a second wire wound around a pulley disposed as a movable pulley in the first intermediate portion by the eccentric member, whereby the pulling and bending of the second intermediate portion is by a third wire connected to the pulley, and a fingertip bending mechanism for pulling and bending the fingertip by a fourth wire connected to the first intermediate portion, whereby the pulling and straightening is by a fifth wire.

12 Claims, 17 Drawing Sheets

FOREIGN PATENT DOCUMENTS

| | | |
|---|---|---|
| JP | A 50-139594 | 11/1975 |
| JP | A 61-500531 | 3/1986 |
| SU | 910410 * | 3/1982 |
| SU | 1161377 A * | 6/1985 |
| SU | 1553381 A1 * | 3/1990 |
| WO | WO 99/13807 | 3/1999 |

* cited by examiner

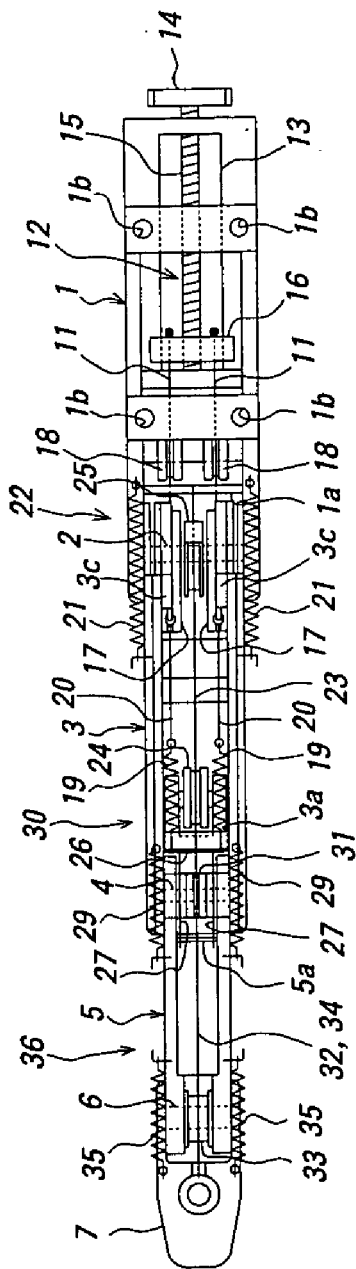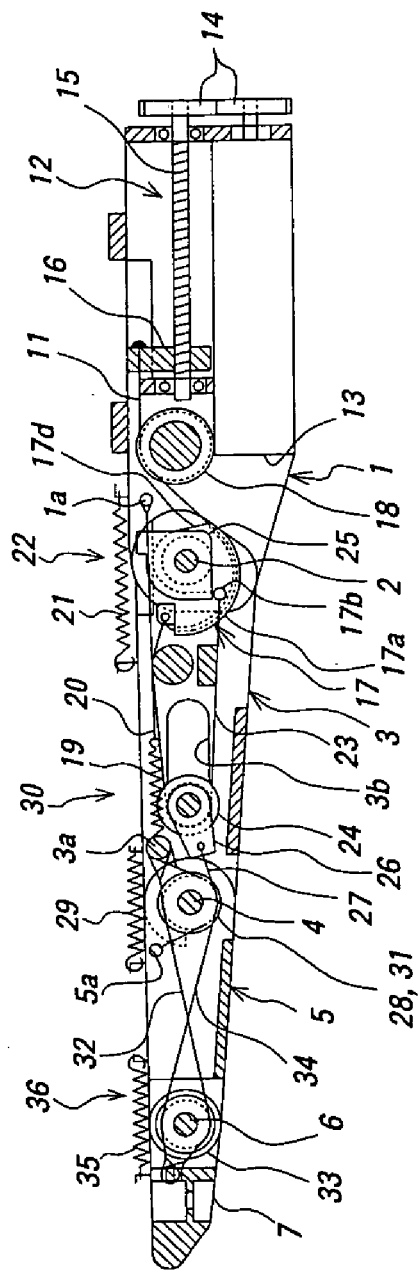

MOVABLE FINGER FOR PROSTHESES, UPPER EXTREMITY PROSTHESES USING THIS MOVABLE FINGER, AND MOVABLE FINGER CONTROLLER

TECHNICAL FIELD

This invention relates to a movable finger for a prosthesis and, more particularly, to a movable finger for an upper extremity prosthesis, an upper extremity prosthesis using the movable finger, and a controller for the movable finger.

BACKGROUND ART

Conventionally, as a movable finger for an upper extremity prosthesis, a movable finger for an active upper extremity prosthesis has generally been known. As to this movable finger, bases of three or five fingers, which are formed to be slightly bent in fixed shapes respectively, are swingably supported on the back or the palm of an upper extremity prosthesis. These fingers are connected to a linkage mechanism provided inside the back and the palm of the hand, a control lead made of wire is set around the back of a person wearing the upper extremity prosthesis, one end of the control lead being connected to the linkage mechanism. The other end of the control lead is connected to an arm of a side opposite to the side of fixing the upper extremity prosthesis. The control lead is pulled or loosened by moving the arm, and accordingly the three or five fingers are bent or returned by simultaneously swinging all the fingers at the bases thereof by the linkage mechanism.

However, the movable finger for an active upper extremity prosthesis cannot perform any operations other than the simple one of simultaneous bending or returning of the three or five fingers by swinging only at their bases. Consequently, there is a problem that the degree of freedom is too low compared with that of a real hand. In addition, since it is necessary to keep the control lead made of wire attached to the back of the person in wearing the upper extremity prosthesis, there is also a problem that uncomfortableness is felt at the back.

DISCLOSURE OF THE INVENTION

It is an object of the present invention to provide a movable finger capable of advantageously solving the foregoing problems. The movable finger for a prosthesis of the invention is for at least one of a plurality of fingers of the prosthesis, and comprises: a base disposed between a back and a palm of a hand, or between an instep and a sole of a foot; a first intermediate portion having a rear end swingably connected to a tip of the base through a first support shaft; a second intermediate portion having a rear end swingably connected to a tip of the first intermediate portion through a second support shaft; and a fingertip having a rear end swingably connected to a tip of the second intermediate portion through a third support shaft. In this case, the movable finger is characterized in that an actuator is disposed in the base to pull one end of a first thin string member; an eccentric member is disposed in a connected portion between the base and the first intermediate portion, the eccentric member being rotatably supported by the first support shaft with respect to the base and the first intermediate portion, and having a winding portion of an inconstant distance from the first support shaft; the first thin string member is passed through a finger inner side of the first support shaft and wound on the winding portion of the eccentric member, the other end of the first thin string member is connected to a portion of the eccentric member on a side where the winding portion is greatly separated from the first support shaft; the portion of the eccentric member is connected to a portion of the first intermediate portion closer to a tip than the first support shaft through a first intermediate portion pulling spring, and a first intermediate portion straightening spring is inserted between the first intermediate portion and the base to always urge or force the first intermediate portion to take a straightened posture with respect to the base, thus constituting a first intermediate portion bending mechanism; a pulley wound with a second thin string member is movably disposed in the first intermediate portion in a longitudinal direction thereof, one end of the second thin string member is connected to the base through a finger outer side of the first support shaft, the other end of the second thin string member is connected to the portion of the eccentric member greatly separated from the first support shaft; one end of a third thin string member, the other end thereof being connected to a support shaft of the pulley, is connected through the finger inner side of the second support shaft to a portion of the second intermediate portion closer to a tip than the second support shaft, and a second intermediate portion straightening spring is inserted between the second intermediate portion and the first intermediate portion to always urge or force the second intermediate portion to take straightened posture with respect to the first intermediate portion, thus constituting a second intermediate portion bending mechanism; one end of a fourth thin string member, the other end thereof being connected through a finger outer side of the second support shaft to the portion of the first intermediate portion closer to the rear end than the second support shaft, is connected through a finger inner side of the third support shaft to a portion of the fingertip closer to a tip than the third support shaft; and one end of a fifth thin string member, the other end thereof being connected through a finger inner side of the second support shaft to the portion of the first intermediate portion closer to the rear end than the second support shaft, is connected through a finger outer side of the third support shaft to a portion of the fingertip closer to a tip than the third support shaft, thus constituting a fingertip bending mechanism.

In the movable finger for a prosthesis of the invention, when the actuator disposed in the base of the first intermediate portion pulls one end of the first thin string member, which is passed through the finger inner side (same side as the palm of the hand) of the eccentric member supported by the first support shaft connecting the base with the first intermediate portion and wound on the winding portion of the eccentric member, and thus draw the first thin string member to the base side, since the other end of the first thin string member is connected to the portion of the eccentric member on a side where the winding portion is greatly separated from the first support shaft, the first thin string member pulls the portion of the eccentric member on the side where the winding portion is greatly separated from the first support shaft to rotate the eccentric member with respect to the base so as to direct the portion toward the finger inner side. Accordingly, the first intermediate portion, where the portion thereof closer to the tip than the first support shaft is connected to the portion of the eccentric member through the first intermediate portion pulling spring, is rotated toward the finger inner side (direction toward the palm of the hand) to take a bend posture with respect to the base while opposing the first intermediate portion straightening spring inserted between the first intermediate portion and the base.

In this case, when no resistance is applied to the rotation of the first intermediate portion, the first intermediate portion is rotated together with the rotation of the eccentric member with respect to the base. Accordingly, at first of rotation, the first thin string member wound on the portion of the winding portion, not greatly separated from the first support shaft, is pulled, resulting in fast rotation of the first intermediate portion. When the first intermediate portion is abutted on a given object to apply resistance to its rotation, the eccentric member is rotated extending the first intermediate portion pulling spring, and the portion of the winding portion of the eccentric member greatly separated from the first support shaft is rotated to the finger inner side. As a result, the driving torque of the first intermediate portion is increased with respect to the same tensile force of the first thin string member, and the first intermediate portion holds down the object by a strong force. If the first intermediate portion is not rotated even by the increased torque, then by the rotation of the eccentric member with respect to the base, only the second intermediate portion and the fingertip are rotated toward the finger inner side as described later.

Further, when the portion of the eccentric member on the side where the winding portion is greatly separated from the first support shaft, is rotated toward the finger inner side, one end of the second thin string member of the second intermediate portion bending mechanism being connected to the portion of the eccentric member, the other end thereof being connected through the finger outer side (the same side as the back of the hand) of the first support shaft to the base, is pulled, thus the pulley wound with the second thin string member thereon is moved in the longitudinal direction of the first intermediate portion to approach the base. One end of the third thin string member, the other end thereof being connected to the support shaft of the pulley, is increased for tension more than the second thin member by the pulley, and passed through the finger inner side of the second support shaft to strongly pull the portion of the second intermediate portion closer to the tip than the second support shaft. Accordingly, the second intermediate portion is rotated toward the finger inner side to take a bent posture with respect to the first intermediate portion while opposing the second intermediate portion straightening spring inserted between the second intermediate portion and the first intermediate portion.

Then, when the second intermediate portion is rotated toward the finger inner side with respect to the first intermediate portion, in the fingertip bending mechanism, one end of the fourth thin string member passed through the finger inner side of the third support shaft, the other end thereof being connected through the finger outer side of the second support shaft to the portion of the first intermediate portion closer to the rear end than the second support shaft, pulls the portion of the fingertip closer to the tip than the third support shaft. Accordingly, the fingertip is rotated toward the finger inner side (toward the palm of the hand) to take a bent posture with respect to the second intermediate portion.

On the other hand, when the actuator disposed in the base loosens one end of the first thin string member to return the first thin string member from a state where the portion of the eccentric member on the side where the winding portion is greatly separated from the first support shaft, is rotated toward the finger inner side, or from a state where the first intermediate portion is thereby rotated and bent with respect to the base, the first intermediate portion straightening spring inserted between the first intermediate portion and the base urges the first intermediate portion by an elastic force. Accordingly, the first intermediate portion is rotated toward the finger outer side so as to take a straightened posture with respect to the base. Then, the first intermediate portion pulling spring inserted between the portion of the first intermediate portion closer to the tip than the first support shaft, and the portion of the eccentric member on the side where the winding portion is greatly separated from the first support shaft, pulls the portion of the eccentric member, and the eccentric member is rotated with respect to the base such that the portion can be rotated toward the finger outer side.

Thus, when the portion of the eccentric member on the side of the winding portion is greatly separated from the first support shaft, is rotated toward the finger outer side, the second thin string member is loosened, and the pulley wound with the second thin string member thereon becomes capable of being moved in the longitudinal direction of the first intermediate portion to approach the fingertip. The third thin string member having one end connected to the support shaft of the pulley is loosened, and the second intermediate portion straightening spring inserted between the second intermediate portion and the first intermediate portion urges the second intermediate portion by an elastic force. Accordingly, the second intermediate portion is rotated toward the finger outer side so as to take a straightened posture with respect to the first intermediate portion.

Then, when the second intermediate portion is rotated to the finger outer side with respect to the first intermediate portion, in the fingertip bending mechanism, one end of the fifth thin string member passed through the finger outer side of the third support shaft, the other end thereof being connected through the finger inner side of the second support shaft to the portion of the first intermediate portion closer to the rear end than the second support shaft, pulls the portion of the fingertip closer to the tip than the third support shaft. Accordingly, the fingertip is rotated toward the finger outer side so as to take a straightened posture with respect to the second intermediate portion.

Therefore, according to the movable finger for a prosthesis of the invention, for each finger, the swinging of the first intermediate portion with respect to the base disposed between the back and the palm of the hand, or between the instep and the sole of the foot, the swinging of the second intermediate portion with respect to the first intermediate portion, and the swinging of the fingertip with respect to the second intermediate portion are carried out in synchronization with one another, by the bending mechanism constructed to be slim and compact so as to be contained within the size of a human finger by using the thin string members. Thus, the finger can be bent and straightened. Moreover, in the case of gripping an object or the like, when the bending rotation of the first intermediate portion receives resistance generated by its abutment on the object, the rotational torque of the first intermediate portion is automatically increased by the eccentric member, making it possible to firmly grip the object. Even when the first intermediate portion is not rotated at all or rotated only slightly and stopped due to resistance, the second intermediate portion and the fingertip are continuously rotated to set the entire finger around the object. Thus, the object can be firmly gripped by the entire finger, being assisted by the action of increasing force by the pulley of the first intermediate portion.

According to the invention, one end of the second thin string member of the second intermediate portion bending mechanism may be connected to the first intermediate portion in place of the eccentric member. In this case, it is not allowed to rotate only the second intermediate portion and the fingertip toward the finger inner side. However, if the first intermediate portion is rotated to a certain extent, the second intermediate portion and the fingertip are rotated in synchronization therewith, the entire finger is set around the object, and thus the object can be firmly gripped, being assisted by the action of increasing force by the pulley of the first intermediate portion.

According to the invention, in the fingertip bending mechanism, instead of or in addition to the fifth thin string member, a fingertip straightening spring may be provided to be inserted between the fingertip and the second intermediate portion to always urge the fingertip to take a straightened posture with respect to the second intermediate portion. Thus, it is possible to bend and straighten the fingertip.

Moreover, according to the invention, the first intermediate portion bending mechanism may include, instead of the eccentric member, a pulley having a winding portion of a constant distance from the first support shaft. Thus, it is possible to provide the foregoing operations and effects except the torque increase of the eccentric member.

The upper extremity prosthesis of the invention comprises: a back of a hand, alternatively a palm of a hand. In this case, the bases of the movable fingers for a prosthesis used for a plurality of fingers excluding a thumb are attached to the back of the hand, alternatively the palm of the hand in a curved arrangement to have a center of curvature in the palm of the hand.

According to the upper extremity prosthesis of the invention, a plurality of movable fingers can be disposed roughly in parallel with each other in straightened states, and the fingertips of the movable fingers can be disposed close to each other in bent states of the fingers. Thus, it is possible to achieve hand finger movements having high resemblance to real ones, such as reception of the object on the palm of the hand, picking of the object by fingertips, and the like, by a degree of movement freedom lower than that for the real hand fingers.

According to the upper extremity prosthesis of the invention, the bases may be attached to the back of the hand, alternatively the palm of the hand in the curved arrangement to be elastically swung. Thus, if the movable fingers are respectively bent and the fingertips are abutted on each other when the fingertips of the movable fingers approach each other, the base is swung to release a pressing force applied to the fingertip by the abutment. As a result, even when the accuracy of attaching position of the base to the back or palm of the hand is not so high, it is possible to prevent damaging caused by the abutments of the fingertips on each other.

The invention provides a movable finger controller for controlling operations of the actuators for a plurality of the movable fingers for a prosthesis. The controller comprises: a plurality of sensors respectively provided in a plurality of places of a body of a human wearing the prosthesis in order to detect an electric signal flowing through the human body by consciousness of moving a plurality of fingers caused by the human; a programmable logic device for receiving signals from the plurality of sensors, learning a combination pattern of the signals based on a genetic algorithm, and outputting an operation command signal according to the combination pattern; and a programmable controller for receiving the operation command signal from the programmable logic device and a changing signal from an operation mode changing means operated by the human wearing the prosthesis, and outputting a driving signal to each of the actuators based on the signals and a program pregiven according to a combination of the signals.

In the movable finger controller, the sensors provided in the plurality of places of the human body wearing the upper extremity prosthesis detect electric signals such as myoelectric signals flowing through the human body by the consciousness of moving the plurality of fingers caused by the human, and output the signals. Then, the programmable logic device receives the signals from the sensors, learns a combination pattern of the signals based on a genetic algorithm, and outputs an operation command signal according to the combination pattern. Then, the programmable controller receives the operation command signal from the programmable logic device and a changing signal from the operation mode changing means operated by the human, and outputs driving signals to the respective actuators of the plurality of movable fingers of the prosthesis based on the received signals and a program pregiven based on the combination of these signals.

Thus, according to the movable finger controller of the invention, only by means of that the human wearing the upper extremity prosthesis is conscious of moving the fingers, the movable fingers of the upper extremity prosthesis can be respectively operated. By making different the overall operational state of the movable fingers based on the combination pattern of the signals from the plurality of sensors, plural kinds of operations such as object gripping, hand opening, pointing, and the like, can be carried out by the upper extremity prosthesis. In addition, the programmable logic device automatically changes the combination of logical circuits based on the genetic algorithm, and learns adaptability between the combination pattern of the signals and the operational state of each movable finger, and output an operation command signal according to the combination pattern of the signals currently outputted from the plurality of sensors. Thus, the controller can learn the combination pattern of the signals within a very short time so as to cause the upper extremity prosthesis to carry out a desired operation.

Furthermore, according to the movable finger controller of the invention, a program of a plurality of operation modes can be provided for one combination pattern beforehand to the programmable controller. Then, by operating the operation mode changing means such as a switch provided on the prosthesis, with respect to e.g. a combination pattern for holding an object, the human wearing the upper extremity prosthesis can switch an operation mode to be currently used among a plurality of operation modes, e.g., the operation mode of a plurality of fingers when a portable telephone set is held, the operation mode of a plurality of fingers when a pencil is held, and so on. Therefore, even if the number of combination pattern of signals from the sensors is small, a complex operation suited to the use condition of the upper extremity prosthesis can be carried out by a plurality of movable fingers. Especially, the plurality of fingers can carry out time-sequential operations, such as successive bending of fingers in operation of the fingers.

BRIEF DESCRIPTION OF THE DRAWINGS

FIG. 1a is a plan view showing a movable finger for a prosthesis according to an embodiment of the present invention.

FIG. 1b is a vertical sectional view of the movable finger for a prosthesis of the embodiment.

BEST MODE OF CARRYING OUT THE INVENTION

Figure 2:
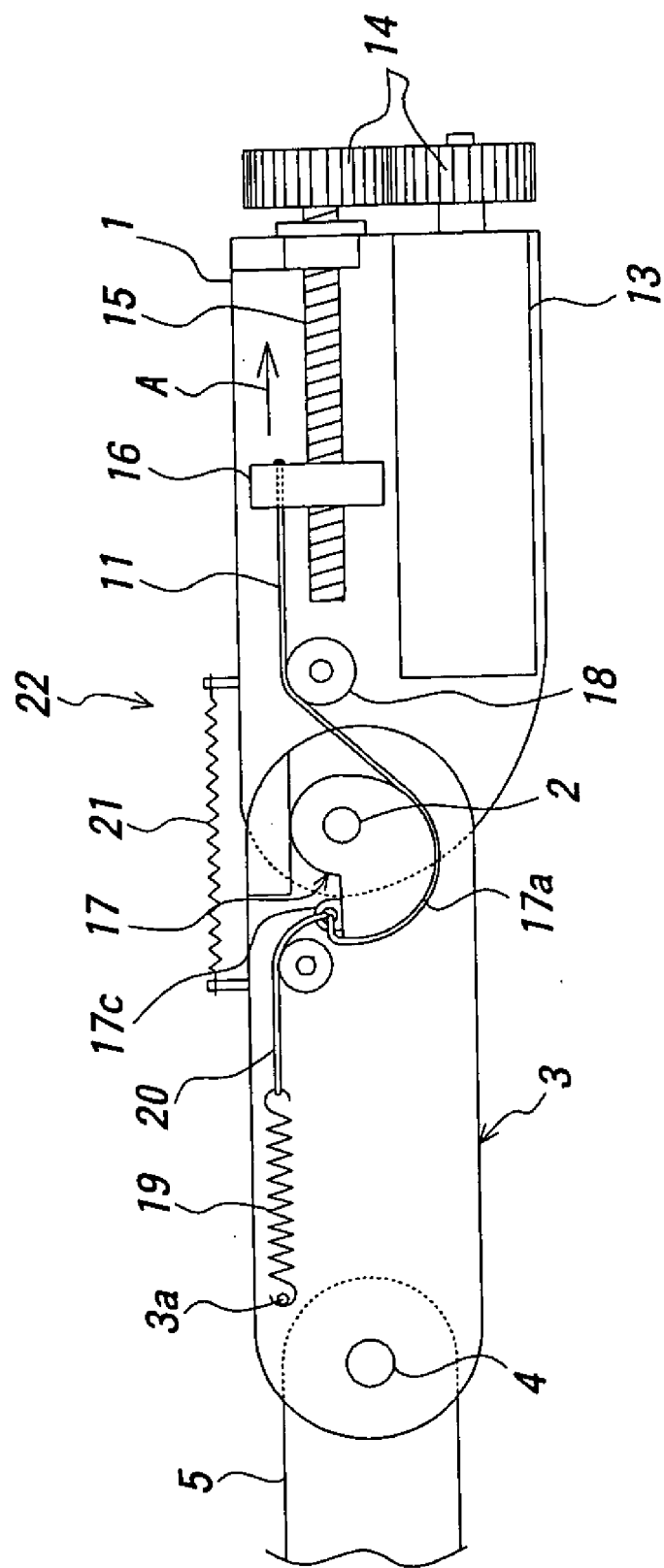
FIG. 2 is an explanation view schematically illustrating a first intermediate portion bending mechanism of the movable finger for a prosthesis of the embodiment.

Next, the mode of the invention will be described in detail by way of embodiment with reference to the accompanying drawings. FIG. 1a is a plan view showing a movable finger for a prosthesis according to an embodiment of the invention; and FIG. 1b is a vertical sectional view of the movable finger for a prosthesis of the embodiment. The movable finger for a prosthesis of the embodiment is used as at least one of a plurality of fingers of an upper extremity prosthesis as a prosthesis, and includes: a base 1 disposed between the back and the palm of a not shown hand; a first intermediate portion 3 having a rear end swingably connected to the tip of the base 1 through a first support shaft 2; a second intermediate portion 5 having a rear end swingably connected to the tip of the first intermediate tip 3 through a second support shaft 4; and a fingertip 7 having a rear end swingably connected to the tip of the second intermediate portion 5 through a third support shaft 6.

The movable finger of the embodiment includes an electric-motorized linear driving device 12 disposed in the base 1 to serve as an actuator for pulling one end of each of two first wires 11 as first thin string members. The electric-motorized linear driving device 12 has an electric servo motor 13 incorporating a rotary encoder, a screw shaft 15 rotatably supported on the base 1 and coupled to be driven to an output shaft of the servo motor 13 through a gear combination 14 as a gear train, and a slider 16 engaged with the screw shaft 15 and slidably fitted to the base 1. One end of each of the two wires 11 is connected to the slider 16.

In the described case, in a connected portion between the base 1 and the first intermediate portion 3, two eccentric members 17 are disposed, which are supported by the first support shaft 2 so as to be rotated with respect to the base 1 and the first intermediate portion 3 and have winding portions 17a inconstant in distances from the first support shaft 2. Each of the first wires 11 is wound on each of pulleys 18 rotatably supported on the base 1, then passed through the finger inner side (lower side in FIG. 1b) of the first support shaft 2 to be wound on the winding portion 17a of each eccentric member 17. The other end of the first wire 11 is connected to the portion of the eccentric member 17 on a side, where the winding portion 17a is separated greatly from the first support shaft 2 (in the rotational position of the eccentric member 17 where the movable finger is straightened as shown in FIGS. 1a and 1b, the portion is located in a direction away from the base 1, i.e., in the left side of the first support shaft 2 in FIGS. 1a and 1b). The above mentioned portion of each eccentric member 17 is connected to a pin 3a fixed to the portion of the first intermediate portion 3 closer to the tip than the first support shaft 2 through a first intermediate portion pulling spring 19 and a connecting wire 20. In addition, between the first intermediate portion 3 and the base 1, a first intermediate portion straightening spring 21 is inserted to always urge the first intermediate portion 3 to take a straightened posture with respect to the base 1 as shown in FIGS. 1a and 1b, thus constituting a first intermediate portion bending mechanism 22.

Further, according to the embodiment, a pulley 24 having a second wire 23 wound as a second thin string member is disposed in the first intermediate portion 3 so as to be moved in the longitudinal direction of the first intermediate portion 3 by being guided by an oblong hole 3b formed in the first intermediate portion 3 to be extended in the longitudinal direction thereof. One end of the second wire 23 is connected to a pin 1a fixed to the base 1, through a guiding hole of a first guiding pulley 25 supported by the first support shaft 2 so as not to be rotated with respect to the base 1, the guiding hole being located in a finger outer side (upper side in FIG. 1b) with respect to the first support shaft 2. The other end of the second wire 23 is connected to a pin 17b fixed to the portion of the eccentric member 17 on a side greatly separated from the first support shaft 2. One end of each of two third wires 27 as third thin string members, the other end thereof being connected to a bracket 26 supporting a support shaft of the pulley 24, is wound on the finger inner side (lower side in FIG. 1b) of each of two second guiding pulleys 28 rotatably supported by the second support shaft 4, and connected to a pin 5a fixed to the portion of the second intermediate portion 5 closer to the tip than the second support shaft 4. In addition, between the second intermediate portion 5 and the first intermediate portion 3, a second intermediate portion straightening spring 29 is inserted to always urge the second intermediate portion 5 to take a straightened posture with respect to the first intermediate portion 3 as shown in FIGS. 1a and 1b, thus constituting a second intermediate portion bending mechanism 30.

In addition, according to the embodiment, one end of a fourth wire 32 as a fourth thin string member wound on the finger outer side (upper side in FIG. 1b) of a third guiding pulley 31, which is disposed between the two second guiding pulleys 28 and rotatably supported by the second support shaft 4, is connected to the pin 3a fixed to the portion of the first intermediate portion 3 closer to the rear end than the second support shaft 4. The other end of the fourth wire 32 is wound on the finger inner side (lower side in FIG. 1b) of a fourth guiding pulley 33, which is rotatably supported by the third support shaft 6, and connected to the portion of the fingertip 7 closer to the tip than the third support shaft 6. Also, one end of a fifth wire 34 as a fifth thin string member wound on the finger inner side (lower side in FIG. 1b) of the third guiding pulley 31 is connected to the pin 3a of the first intermediate portion 3. The other end of the fifth wire 34 is wound on the finger outer side (upper side in FIG. 1b) of the fourth guiding pulley 33 and connected to the portion of the fingertip 7 closer to the tip than the third support shaft 6. Further, between the fingertip 7 and the second intermediate portion 5, a fingertip straightening spring 35 is provided to always urge the fingertip 7 to take a straightened posture with respect to the second intermediate portion 5 as shown in FIGS. 1a and 1b, thus constituting a fingertip bending mechanism 36.

FIG. 2 schematically shows the first intermediate portion bending mechanism 22 of the movable finger for a prosthesis of the embodiment. When the slider 16 of the electric-motorized linear driving device 12 disposed in the base 1 is moved right as indicated by an arrow A in FIG. 2 by the rotation of the screw shaft 15 realized by the operation of the servo motor 13, one end of the first wire 11, which is passed through the finger inner side (same side as that of the palm of the hand, i.e. lower side in FIG. 2) of the eccentric member 17 supported by the first support shaft 2 connecting the base 1 with the first intermediate portion 3, is pulled to draw the first wire 11 into the base 1 side. Since the other end of the first wire 11 is connected to the portion 17c (left portion of the first support shaft 2 in FIG. 2) of the eccentric member 17 on the side, where the winding portion 17a is greatly separated from the first support shaft 2, the first wire 11 then pulls the portion 17c of the eccentric member 17 on the side, where the winding portion 17a is greatly separated from the first support shaft 2, to rotate the eccentric member 17 with respect to the base 1 so as to direct the portion 17c to the finger inner side. As a result, the first intermediate portion 3 having a portion closer to the tip than the first support shaft 2, the portion being connected to the portion 17c of the eccentric member 17 through the first intermediate portion pulling spring 19 and the connecting wire 20, is rotated toward the finger inner side (toward the palm of the hand) so as to take a bent posture with respect to the base 1 while opposing the first intermediate portion straightening spring 21 inserted between the first intermediate portion 3 and the base 1.

Figure 3A:
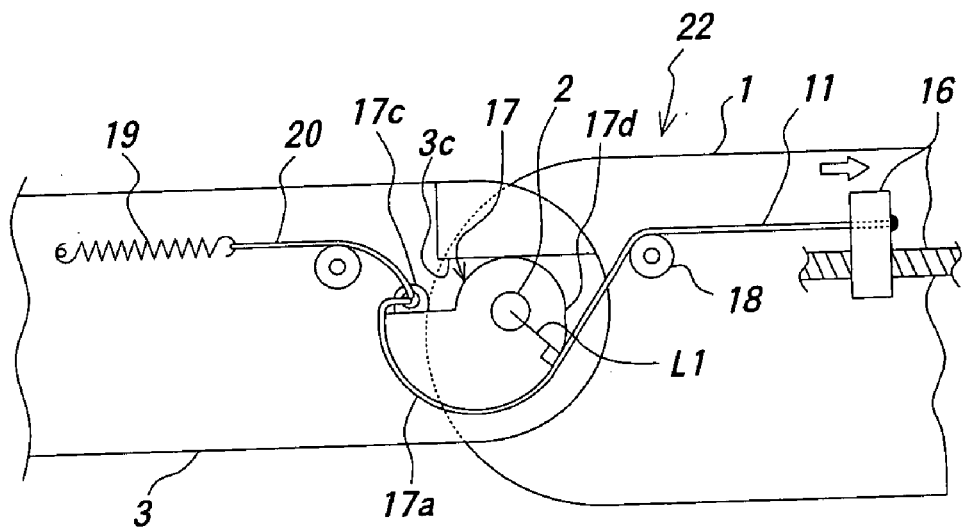
FIGS. 3a and 3b are explanation views, each thereof schematically illustrating an operation of the first intermediate portion bending mechanism.
Figure 4:
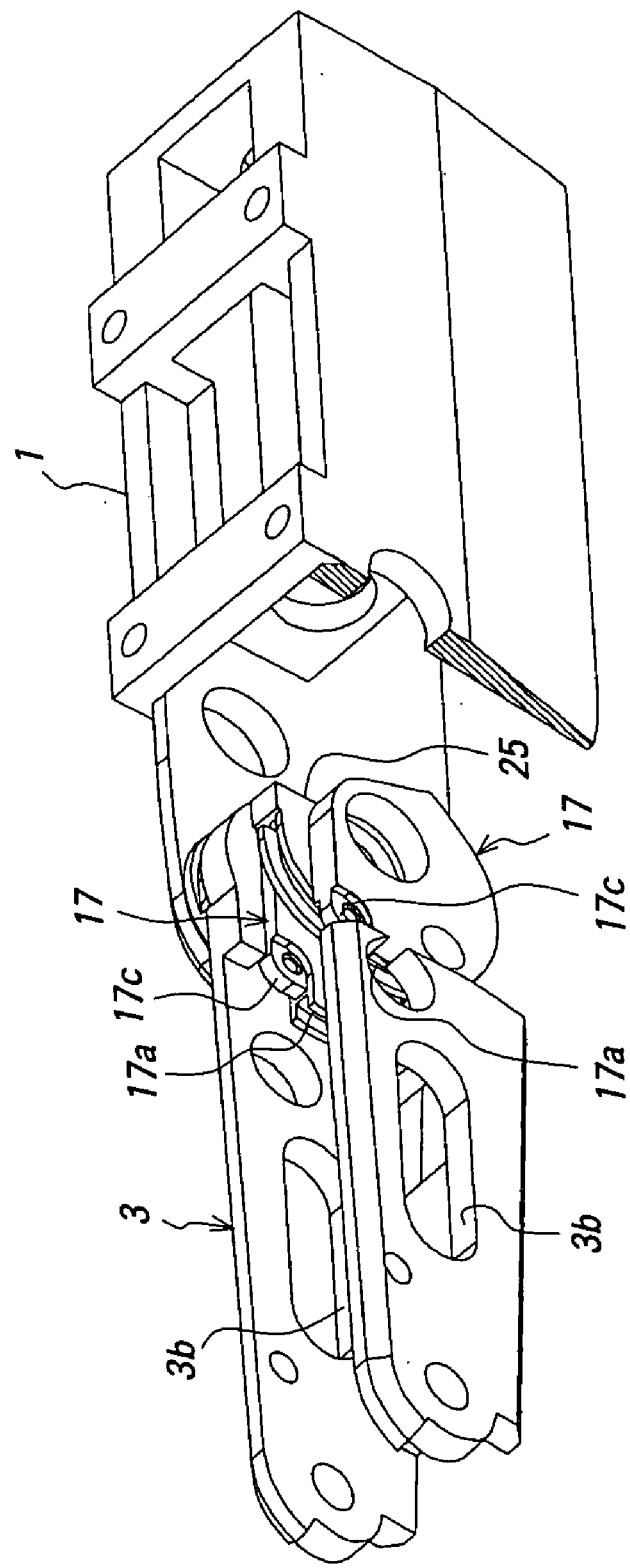
FIG. 4 is a perspective view showing an operation state of the first intermediate portion bending mechanism.
Figure 5:
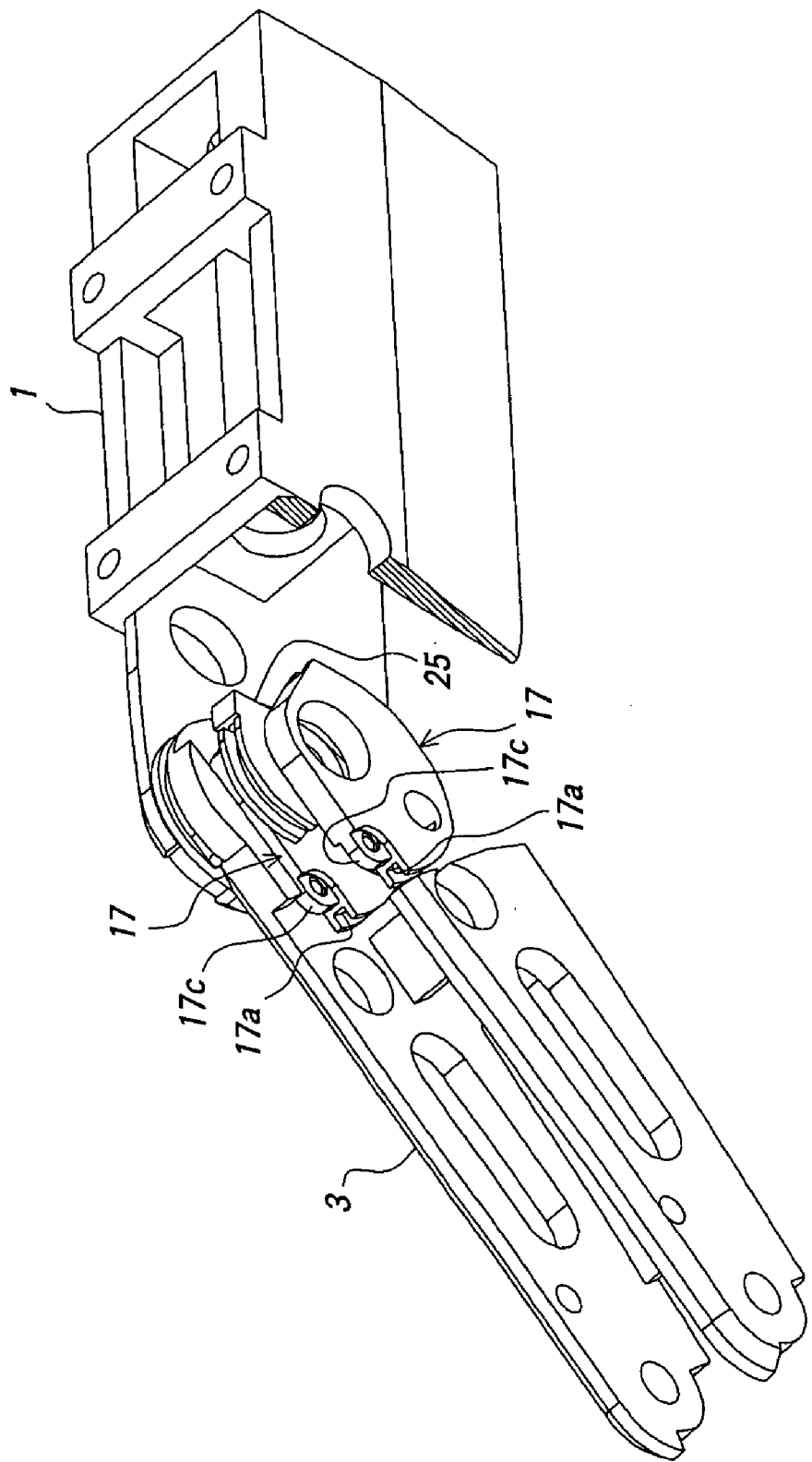
FIG. 5 is a perspective view showing an operation state of the first intermediate portion bending mechanism.

FIGS. 4 and 5 are perspective views, each thereof showing only the base 1, the first intermediate portion 3, the eccentric member 17, and the first guiding pulley 25 in the movable finger of the embodiment, which shows a partially cut away of the base 1 and the first intermediate portion 3. Specifically, FIG. 4 shows an initial straightened state of the first intermediate portion 3 with respect to the base 1 as shown in FIGS. 1a, 1b and 2; and FIG. 5 shows a bent state of the first intermediate portion 3 with respect to the base 1 by rotation of the eccentric member 17, which is realized because the first intermediate portion 3 is not abutted on any objects and does not receive any resistance. When no resistance is applied to the rotation of the first intermediate portion 3 as stated above, the first intermediate portion 3 is rotated together with the eccentric member 17 with respect to the base 1. Accordingly, as shown in FIG. 3a, initially in the rotated state, the first wire 11 wound on the portion (portion of a distance L1) of the winding portion 17a, which is not greatly separated from the first support shaft 2, is pulled, resulting in faster rotation of the first intermediate portion 3.

Figure 3B:
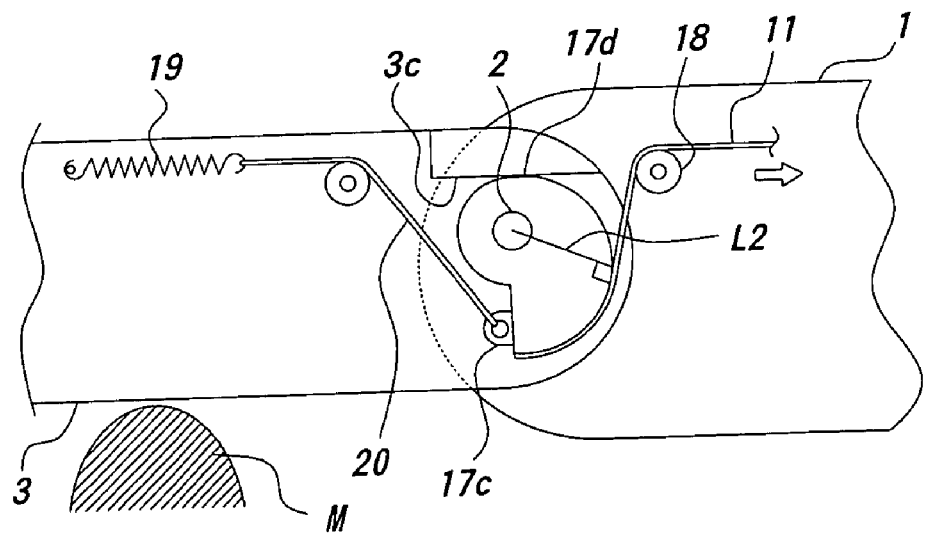

On the other hand, as shown in FIG. 3b, when the first intermediate portion 3 is abutted on a given object M and resistance is applied to the rotation, the eccentric member 17 is rotated while stretching the first intermediate portion pulling spring 19, and the portion (portion of a distance L2) of the winding portion of the eccentric member 11 greatly separated from the first support shaft 2 is rotated to the finger inner side. As a result, the driving torque of the first intermediate portion 3 is increased with respect to the same tensile force of the first wire 11, and the first intermediate portion 3 presses the object M by a strong force corresponding to the extension of the first intermediate portion pulling spring 19. If the first intermediate portion 3 is not rotated even by the increased torque, then by the rotation of the eccentric member 17 with respect to the base 1, only the second intermediate portion 5 and the fingertip 7 are rotated toward the finger inner side to a certain extent as described later with reference to FIG. 8b. However, as shown in FIGS. 1b and 3a, a flat portion 17d is formed in the eccentric member 17, and an abutting portion 3c is protrudingly formed in the first intermediate portion 3. Thus, when the eccentric member 17 is rotated to a certain extent with respect to the first intermediate portion 3, the flat portion 17d of the eccentric member 17 is abutted on the abutting portion 3c of the first intermediate portion 3 as shown in FIG. 3b, and thereafter the eccentric member 17 forcibly rotates the first intermediate portion 3.

Figure 6:
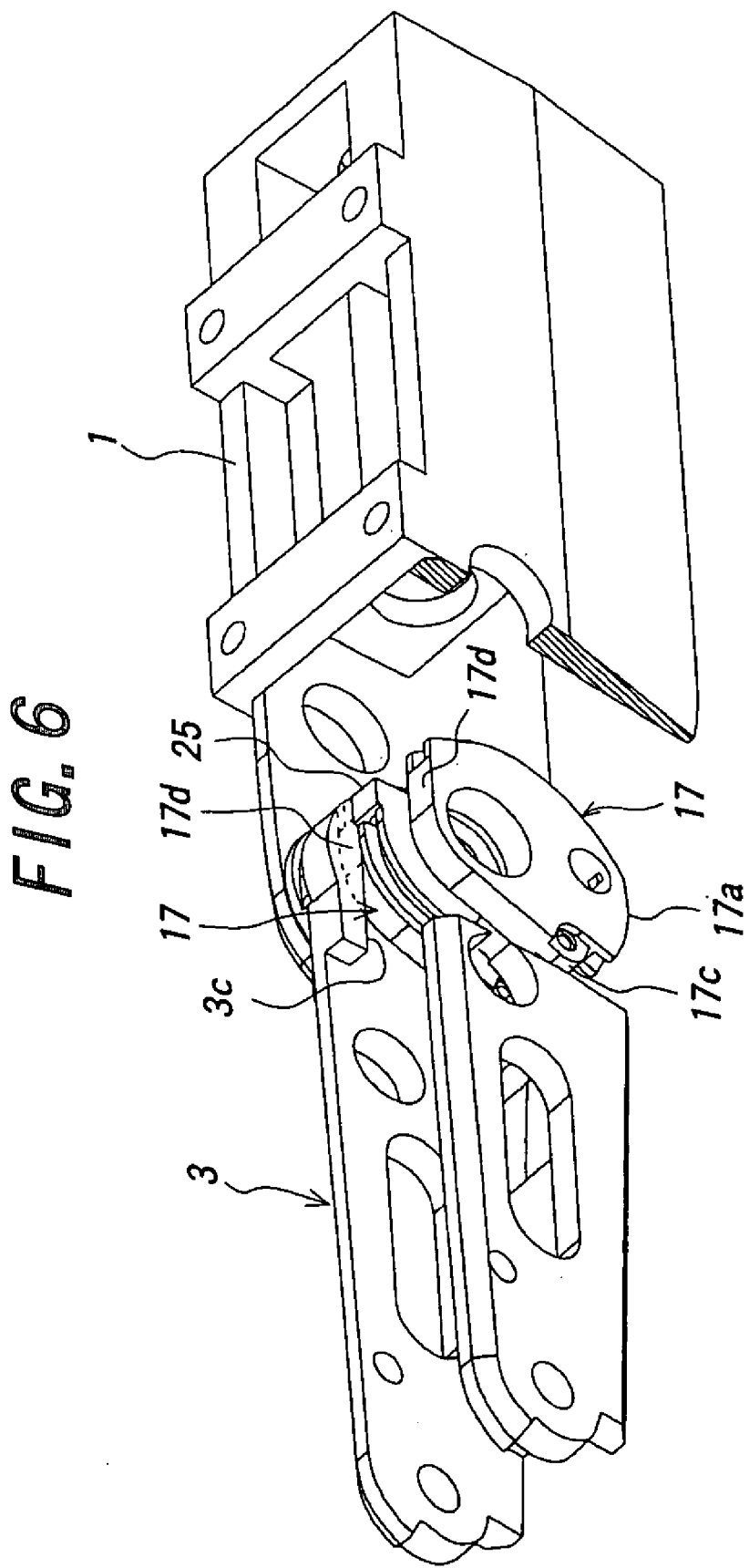
FIG. 6 is a perspective view showing an operation state of the first intermediate portion bending mechanism.

Similarly to FIGS. 4 and 5, FIGS. 6 and 7 are perspective views, each thereof showing only the base 1, the first intermediate portion 3, the eccentric member 17, and the first guiding pulley 25 in the movable finger of the embodiment, partially cutting away the base 1 and the first intermediate portion 3. Specifically, FIG. 6 shows a state shown in FIG. 3b that only the eccentric member 17 is rotated while the first intermediate portion 3 is not rotated; and FIG. 7 a bent state of the first intermediate portion 3 with respect to the base 1, which is set by abutting the flat portion 17d of the eccentric member 17 on the abutting portion 3c of the first intermediate portion 3 and forcibly rotating the first intermediate portion 3 by the eccentric member 17.

Figure 8A:
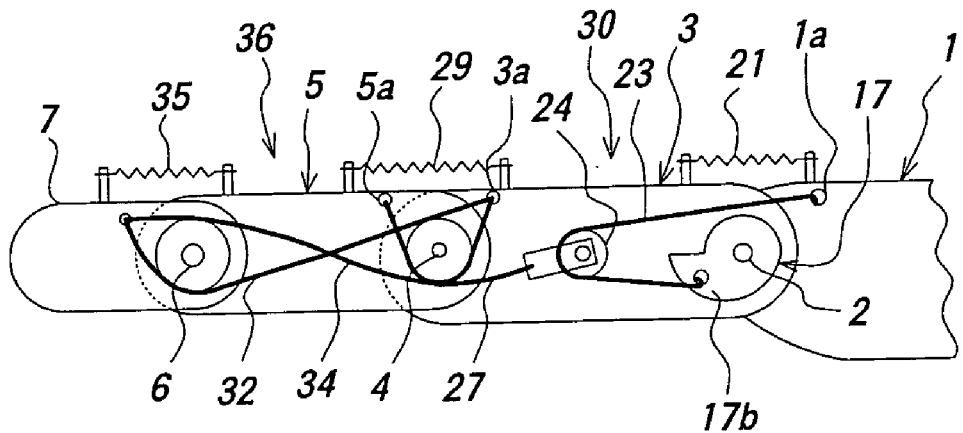
FIGS. 8a and 8b are explanation views, each thereof schematically illustrating a second intermediate portion bending mechanism and a fingertip bending mechanism of the movable finger for a prosthesis of the embodiment.
Figure 8B:
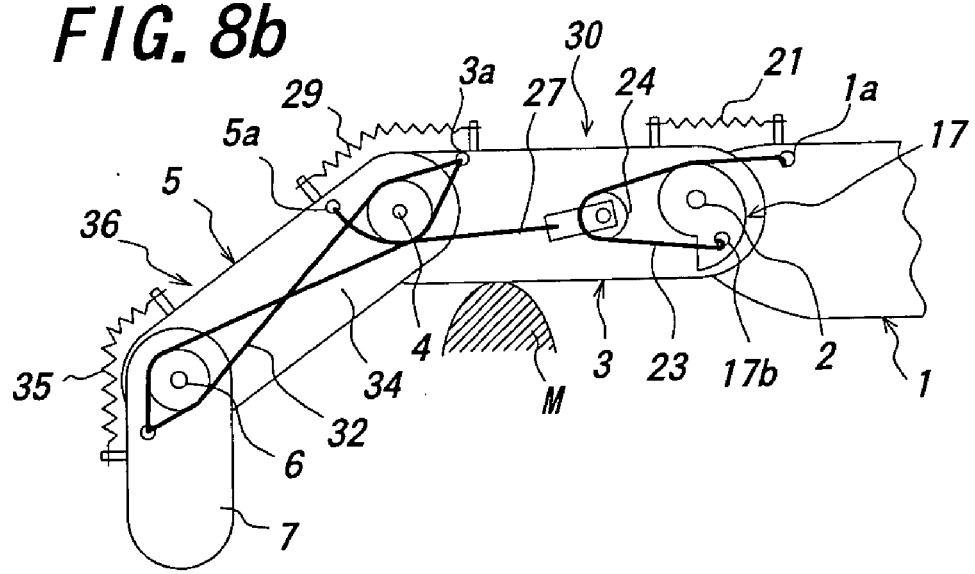

FIG. 8a schematically shows the second intermediate portion bending mechanism 30 and the fingertip bending mechanism 36 of the movable finger for a prosthesis of the embodiment in a state where the second intermediate portion 5 is straightened with respect to the first intermediate portion 3, and the fingertip 7 is straightened with respect to the second intermediate portion 5; FIG. 8b schematically shows the second intermediate portion bending mechanism 30 and the fingertip bending mechanism 36 in a state where the second intermediate portion 5 is rotated to be bent with respect to the first intermediate portion 3, and the fingertip 7 is rotated to be bent with respect to the second intermediate portion 5. As described above, when the portion 17c of the eccentric member 17 on the side, where the winding portion 17a is greatly separated from the first support shaft 2, is rotated toward the finger inner side, one end of the second wire 23 connected to a pin 17b fixed to the portion on the side where the winding portion 17a of the eccentric member 17 is greatly separated from the first support shaft 2, is pulled, the other end of the second wire 23 being connected through the finger outer side (the same side as the back of the hand) of the first support shaft 2 to the base 1. As a result, as shown in FIG. 8b, the pulley 24 having the second wire 23 wound thereon is moved in the longitudinal direction of the first intermediate portion 3 to approach the base 1, thus causing the pulley 24 to function as a movable pulley. One end of the third wire 27, the other end thereof being connected to the support shaft of the pulley 24, is increased in tension more than the second wire 23 by the pulley 24, and then strongly pulls a pin 5a fixed to the portion of the second intermediate portion 5 closer to the tip than the second support shaft 4 through the finger inner side of the second support shaft 4. Accordingly, the second intermediate portion 5 is rotated toward the finger inner side to take a bent posture with respect to the first intermediate portion 3 while opposing the second intermediate portion straightening spring 29 inserted between the second intermediate portion 5 and the first intermediate portion 3.

Then, when the second intermediate portion 5 is rotated toward the finger inner side with respect to the first intermediate portion 3, one end of the fourth wire 32 passed through the finger inner side of the third support shaft 6, the other end thereof being connected through the finger outer side of the second support shaft 4 to the pin 3a fixed to the portion of the first intermediate portion 3 closer to the rear end than the second support shaft 4, pulls the portion of the fingertip 7 closer to the tip than the third support shaft 6. Accordingly, as shown in FIG. 8b, the fingertip 7 is rotated toward the finger inner side (toward the palm of the hand) to take a bent posture with respect to the second intermediate portion 5 while opposing the fingertip straightening spring 35 inserted between the fingertip 7 and the second intermediate portion 5.

Figure 7:
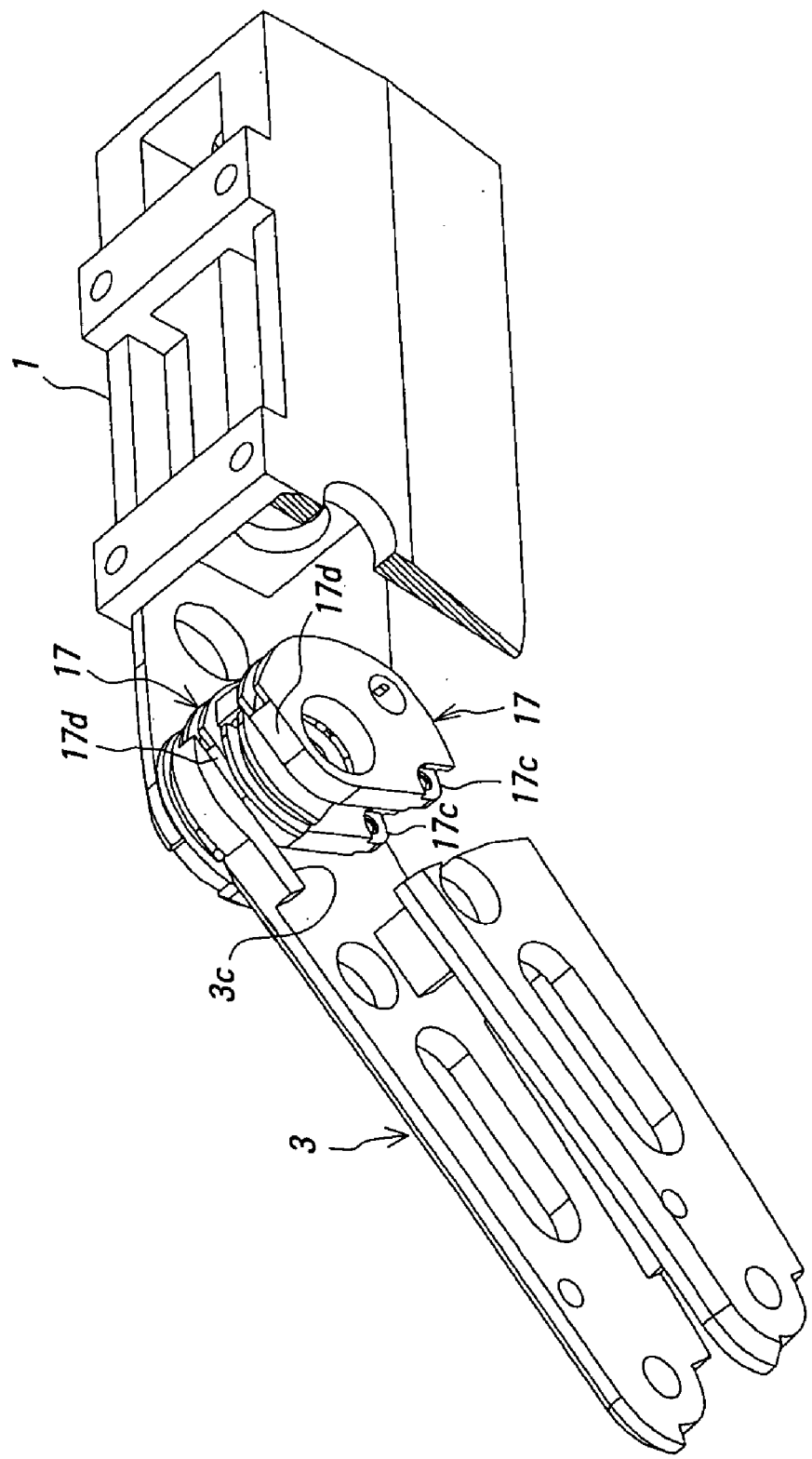
FIG. 7 is a perspective view showing an operation state of the first intermediate portion bending mechanism.

On the other hand, when the slider 16 of the electric-motorized linear driving device 12 disposed in the base 1 is moved in a direction opposite to the above from a state like that shown in FIG. 6 where the portion 17c of the eccentric member 17 on the side, where the winding portion 17a is greatly separated from the first support shaft 2, is rotated toward the finger inner side, or from a state like that shown in FIG. 5 or FIG. 7 where the first intermediate portion 3 is thereby rotated and bent with respect to the base 1, one end of the first wire 11 is loosened to return the first wire 11 to the first intermediate portion 3 side, and the first intermediate portion straightening spring 21 inserted between the first intermediate portion 3 and the base 1 urges the first intermediate portion 3 by an elastic force. Accordingly, the first intermediate portion 3 is rotated toward the finger outer side so as to take a straightened posture with respect to the base 1 as shown in FIGS. 1a and 1b and FIG. 4. Then, the first intermediate portion pulling spring 19, which is inserted between the pin 3a in the portion of the first intermediate portion 3 closer to the tip than the first support shaft 2 and the portion 17c of the eccentric member 17 on the side, where the winding portion 17a is greatly separated from the first support shaft 2, pulls the portion 17c of the eccentric member 17, and the eccentric member 17 is rotated with respect to the base 1 such that the portion 17c can be rotated toward the finger outer side to return to the original position thereof.

When the portion 17c of the eccentric member 17 on the side, where the winding portion 17a is greatly separated from the first support shaft 2, is thus rotated toward the finger outer side, the second wire 23 is loosened, and the pulley 24 having the second wire 23 wound thereon can be moved in the longitudinal direction of the first intermediate portion 3 to approach the fingertip 7. The third wire 27 having one end connected to the support shaft of the pulley 24 is loosened, and the second intermediate portion straightening spring 29 inserted between the second intermediate portion 5 and the first intermediate portion 3 urges the second intermediate portion 5 by an elastic force. Accordingly, the second intermediate portion 5 is rotated toward the finger outer side so as to take a straightened posture with respect to the first intermediate portion 3 as shown in FIGS. 1a and 1b.

Then, when the second intermediate portion 5 is rotated to the finger outer side with respect to the first intermediate portion 3, one end of the fifth wire 34 passed through the finger outer side of the third support shaft 6, the other end thereof being connected through the finger inner side of the second support shaft 4 to the pin 3a fixed to the portion of the first intermediate portion 3 closer to the rear end than the second support shaft 4, pulls the portion of the fingertip 7 closer to the tip than the third support shaft 6. Accordingly, the fingertip 7 is rotated toward the finger outer side so as to take a straightened posture with respect to the second intermediate portion 5 as shown in FIGS. 1a and 1b.

Therefore, according to the movable finger for a prosthesis of the embodiment, for each finger, the swinging of the first intermediate portion 3 with respect to the base 1 disposed between the back and the palm of the hand, the swinging of the second intermediate portion 5 with respect to the first intermediate portion 3, and the swinging of the fingertip 7 with respect to the second intermediate portion 5 are carried out in synchronization with one another, by the bending mechanism constructed to be slim and compact so as to be within the size of a human finger by using the wires. Thus, the finger can be bent and straightened. Moreover, in the case of gripping an object or the like, when the bending rotation of the first intermediate portion 3 receives resistance generated by abutment on the object, the rotational torque of the first intermediate portion 3 is automatically increased by the eccentric member 17, making it possible to firmly grip the object. Even when the first intermediate portion 3 is not rotated at all or slightly rotated to stop due to resistance, only the second intermediate portion 5 and the fingertip 7 are continuously rotated to set the entire finger around the object. Thus, the object can be firmly gripped by the entire finger, being assisted by an action of increasing force by the pulley 24 of the first intermediate portion 3.

Figure 9:
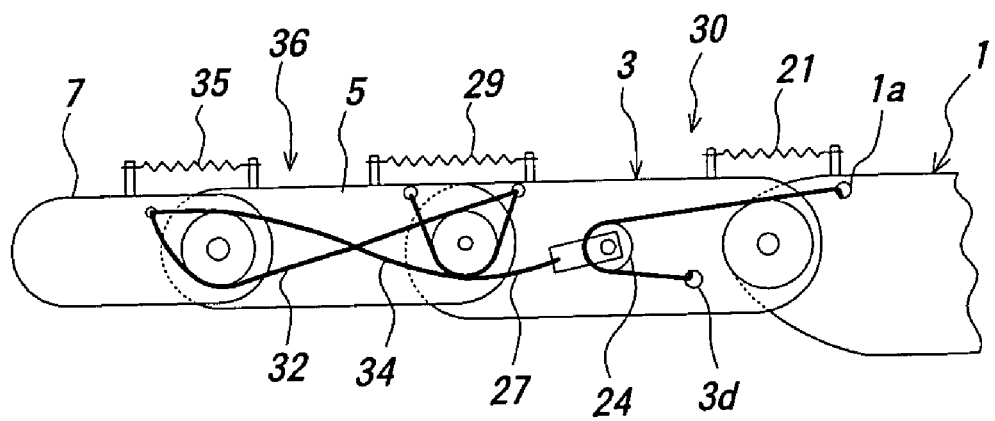
FIG. 9 is an explanation view showing a modified example of the movable finger for a prosthesis of the embodiment.

FIG. 9 schematically shows a modified example of the movable finger for a prosthesis of the foregoing embodiment. In the modified example, one end of the second wire 23 of the second intermediate portion bending mechanism 30 is connected to a pin 3d fixed to the first intermediate portion 3 in place of the eccentric member 17. In the modified example, it is not allowed to rotate only the second intermediate portion 5 and the fingertip 7 toward the finger inner side. However, if the first intermediate portion 3 is rotated to a certain extent, the second intermediate portion 5 and the fingertip 7 can be rotated in synchronization therewith, the entire finger is set around the object, and thus the object can be firmly gripped, being assisted by the action of increasing force by the pulley 24 of the first intermediate portion 3.

Figure 10:
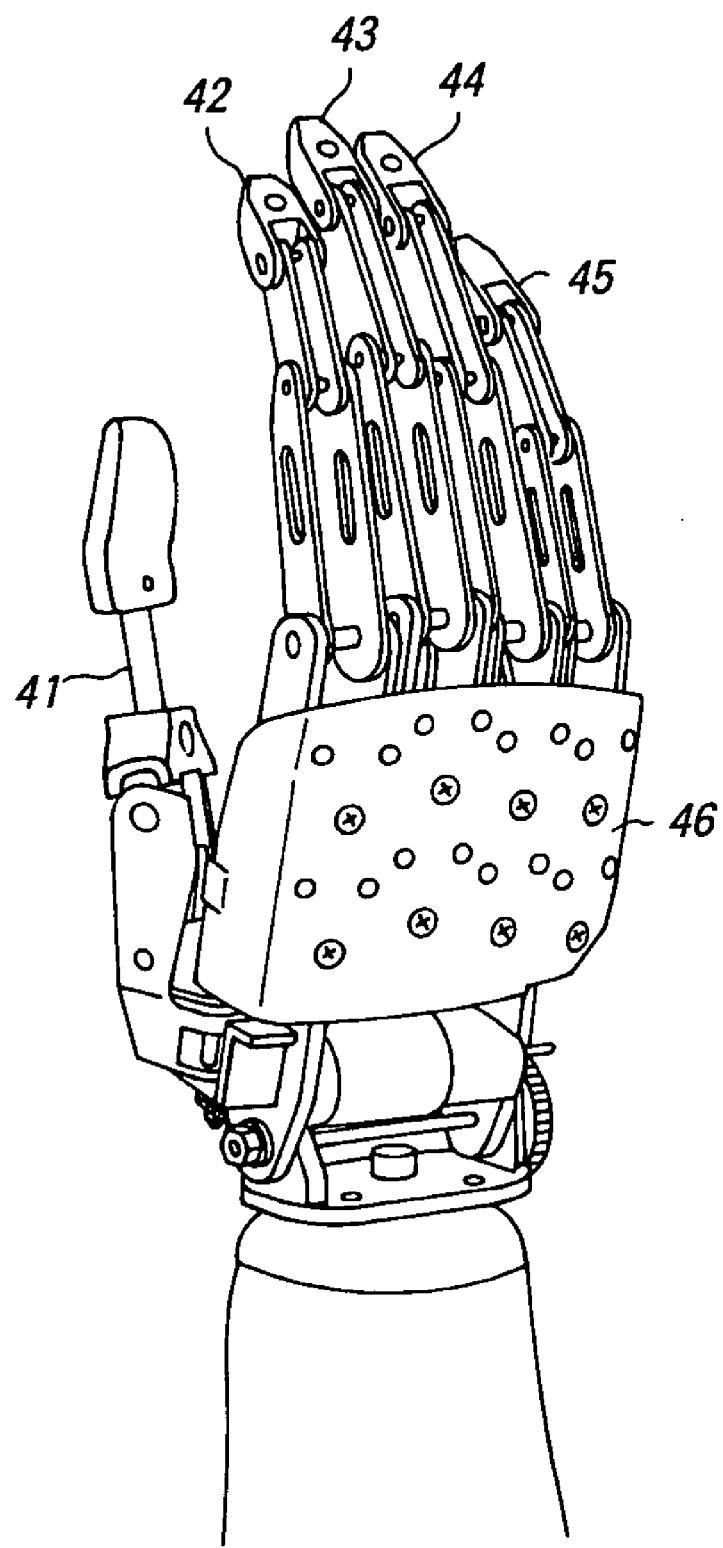
FIG. 10 is a perspective view showing an example of an upper extremity prosthesis, to which the movable finger of the embodiment is applied, when seen from a back side of a hand.
Figure 11:
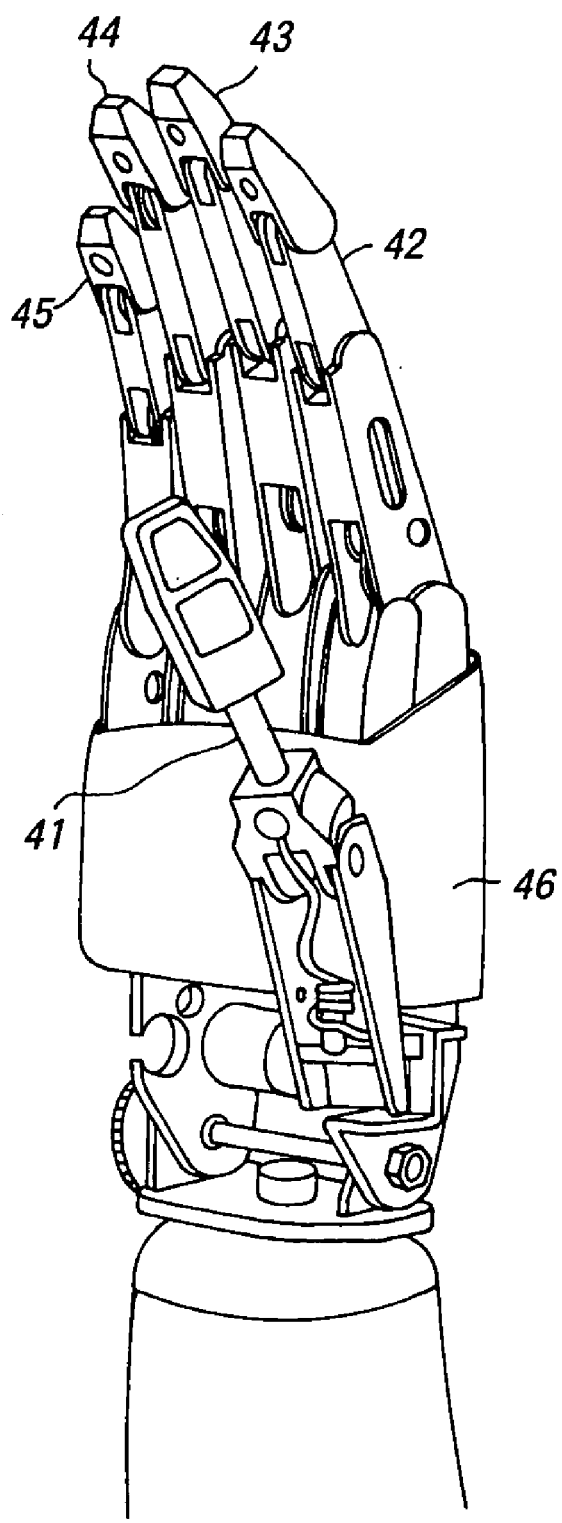
FIG. 11 is a perspective view of the upper extremity prosthesis of the applied example when seen from a palm side of the hand.
Figure 12:
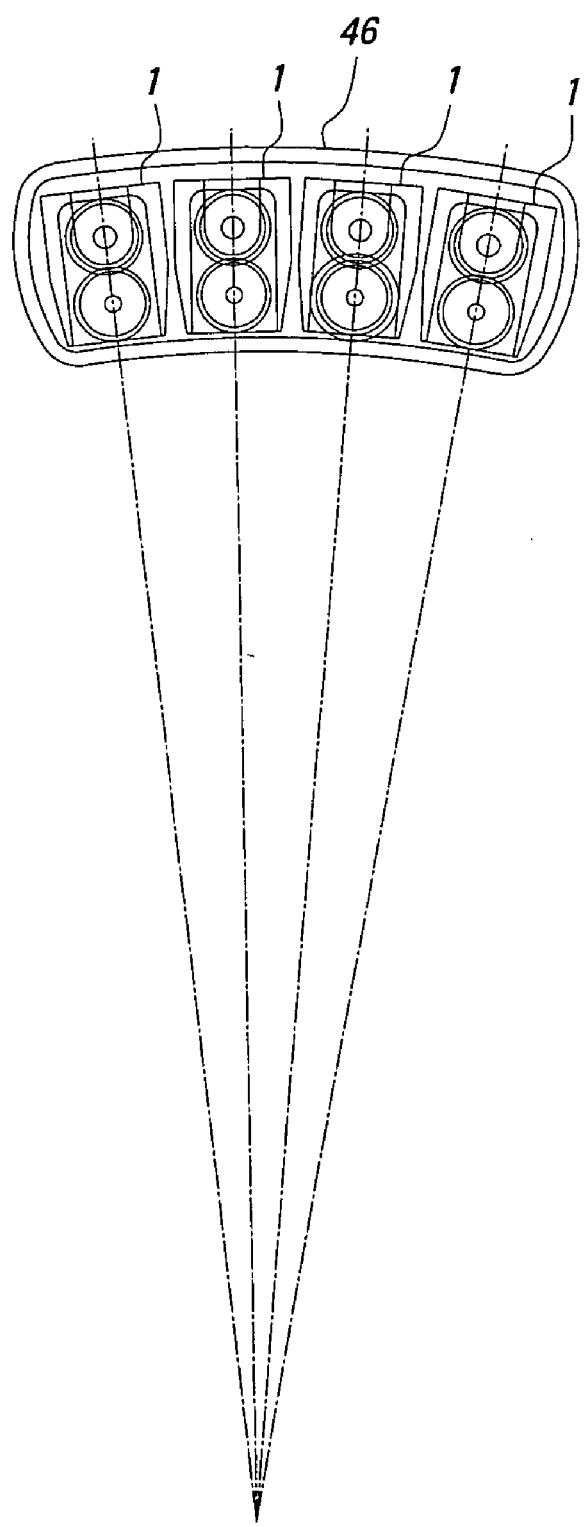
FIG. 12 is an explanation view illustrating an arrangement of bases in a sleeve of the upper extremity prosthesis of the applied example.

FIGS. 10 and 11 are perspective views, each thereof showing an example of an upper extremity prosthesis or a prosthetic hand, to which the movable finger of the embodiment is applied, when seen from the back side or the palm side of the hand. For the upper extremity prosthesis of the applied example, four fingers excluding a thumb 41, i.e., a forefinger 42, a middle finger 43, a ring finger 44 and a little finger 45, are set as movable fingers of the embodiment, and the bases 1 of the movable fingers are housed in a sleeve 46 of a square-cylindrical section, which is slightly curved to have a center of curvature in the palm side of the hand and forms the back and the palm portions of the upper extremity prosthesis, by respectively having spaces around and being arranged to match the curved shapes of the back and the palm portions of the hand, as shown in FIG. 12. In FIGS. 10 and 11, respective bending mechanisms are omitted.

Figure 13A:
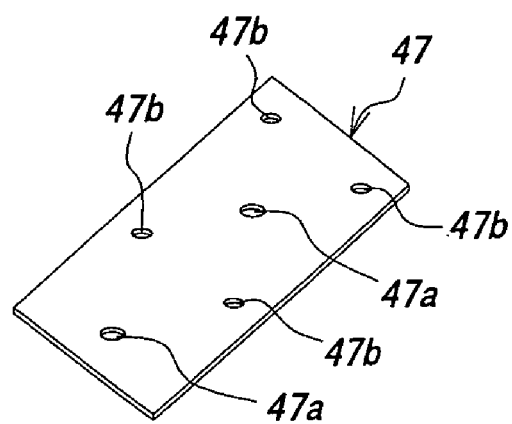
FIGS. 13a and 13b are explanation views, each thereof illustrating a method of attaching each base to the sleeve.
Figure 13B:
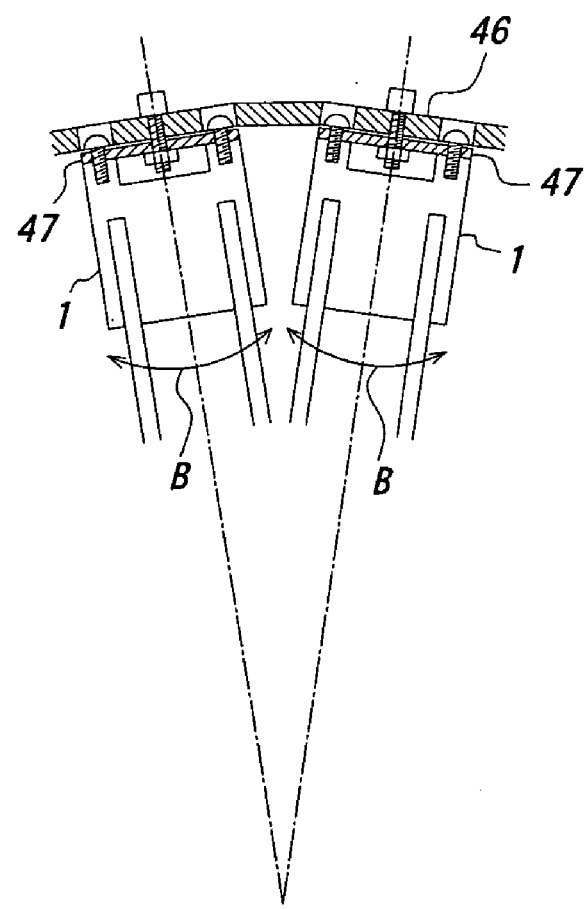

FIGS. 13a and 13b show a method of attaching the base 1 to the sleeve 46. In this case, as shown in FIG. 13a, attaching holes 47a to the sleeve 46 are bored in the center of a spring plate 47, and attaching holes 47b to the base 1 are bored in both sides of the spring plate 47. As shown in FIG. 13b, the spring plate 47 is attached to the sleeve 46 through the attaching holes 47a in the center of the spring plate 47, and the spring plate 47 is attached to the base through the attaching holes 47b in both sides of the spring plate 47. Thus, because the base 1 and each movable finger can be elastically swung with respect to the sleeve 46, as indicated by arrows B in FIG. 13b, by the flexure of the spring plate 47, the fingertips can escape each other a little, and also be gathered while releasing a pressing force generated by the abutment, even if the fingertips are abut on each other when shutting the prosthetic hand. Therefore, it is possible to prevent damage caused by the mutual abutments of the fingertips of the movable fingers even when the accuracy of the attaching position of the base 1 to the sleeve 46 is not so high, and to flexibly match the movable fingers with the shape of the gripped object.

In addition, the thumb 41 of the upper extremity prosthesis of the applied example is provided with a base swingably supported by a support shaft extended roughly in parallel to the bases 1 of the other fingers 42 to 45, and a fingertip swingably supported on the base. The base is swung around the support shaft by a not-shown swing driving device provided in the sleeve 46 and driven by a not-shown normal electric servo motor. The fingertip is swung in directions toward and away from the other fingers 42 to 45 by a not-shown wire pulled by a linear driving device similar to the above-described electric-motorized linear driving device 12, and a not-shown spring provided in the base. Accordingly, the thumb 41 can function as a movable finger.

Figure 14:
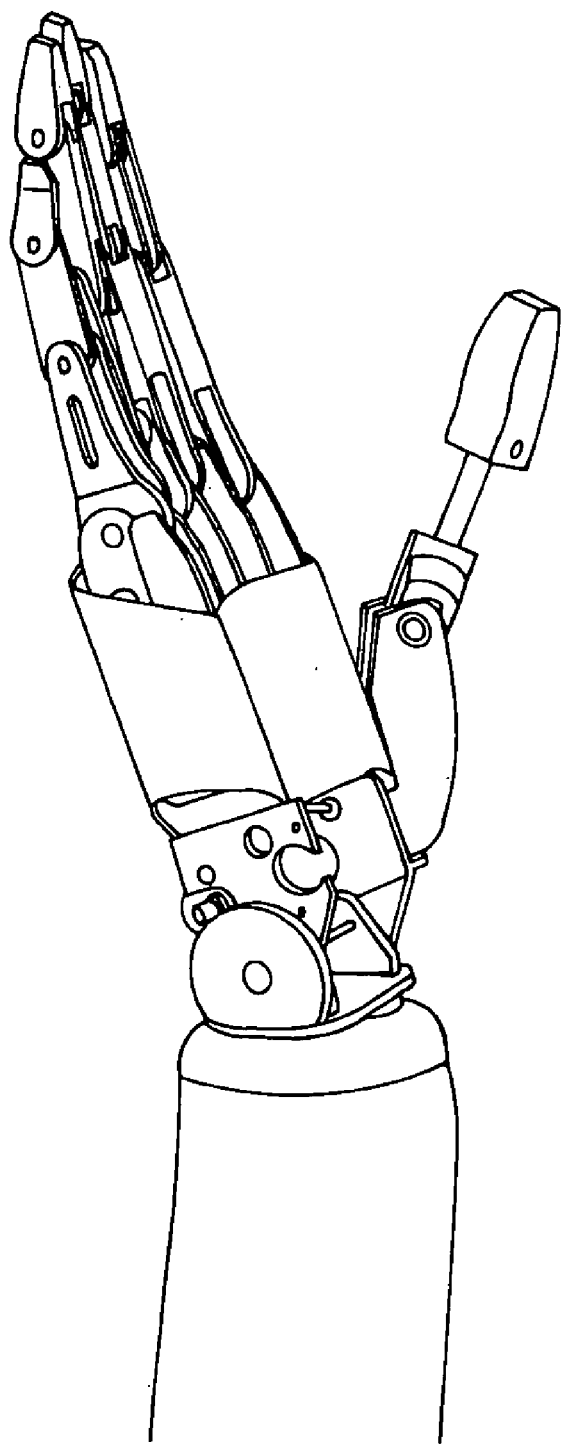
FIG. 14 is a perspective view showing an operation state of the upper extremity prosthesis of the applied example.
Figure 15:
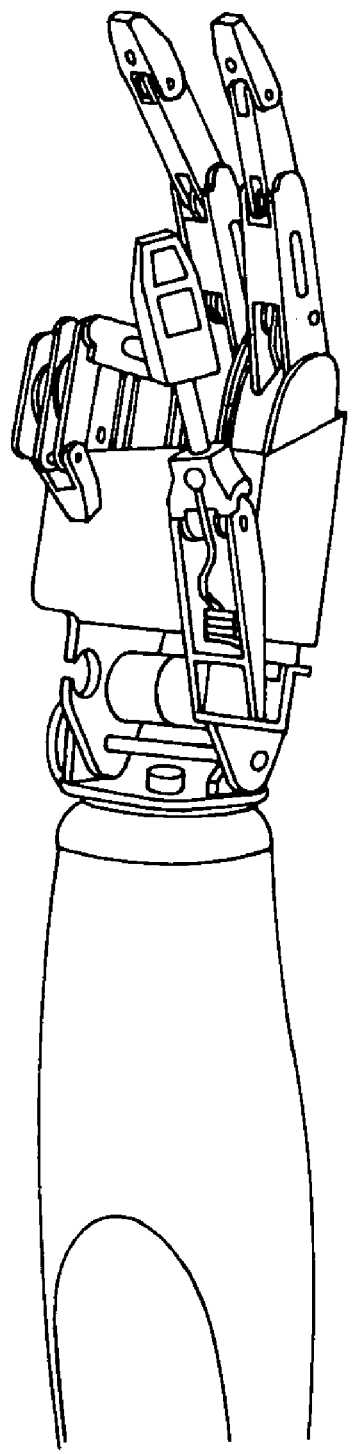
FIG. 15 is a perspective view showing an operation state of the upper extremity prosthesis of the applied example.
Figure 16:
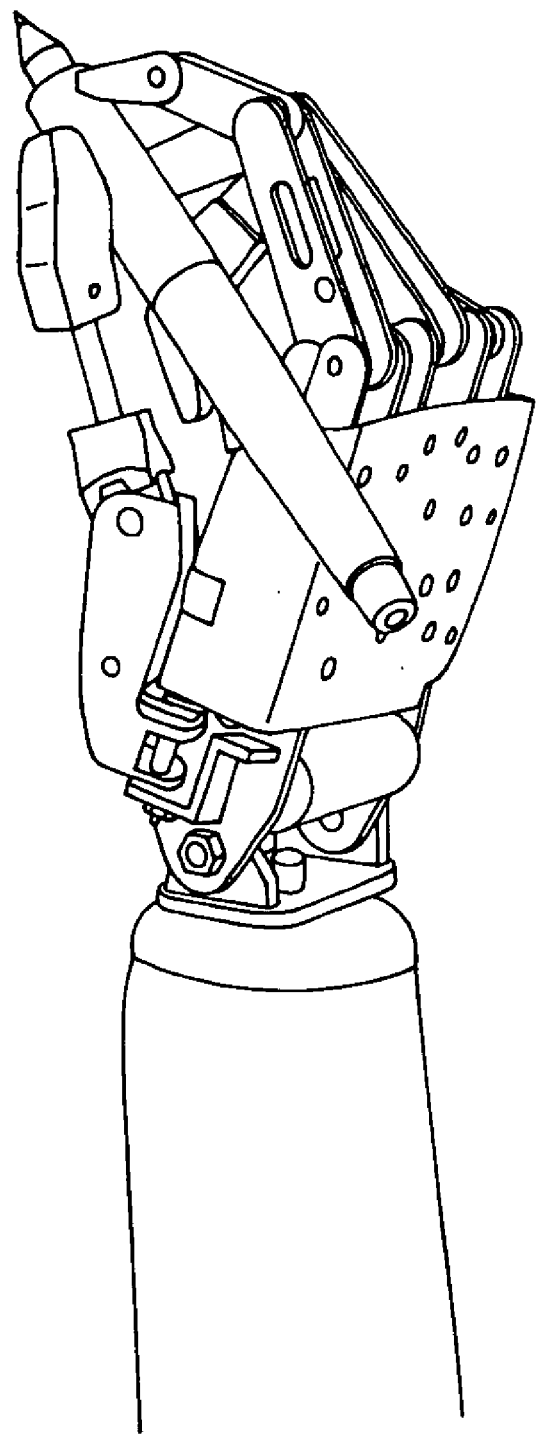
FIG. 16 is a perspective view showing an operation state of the upper extremity prosthesis of the applied example.
Figure 17:
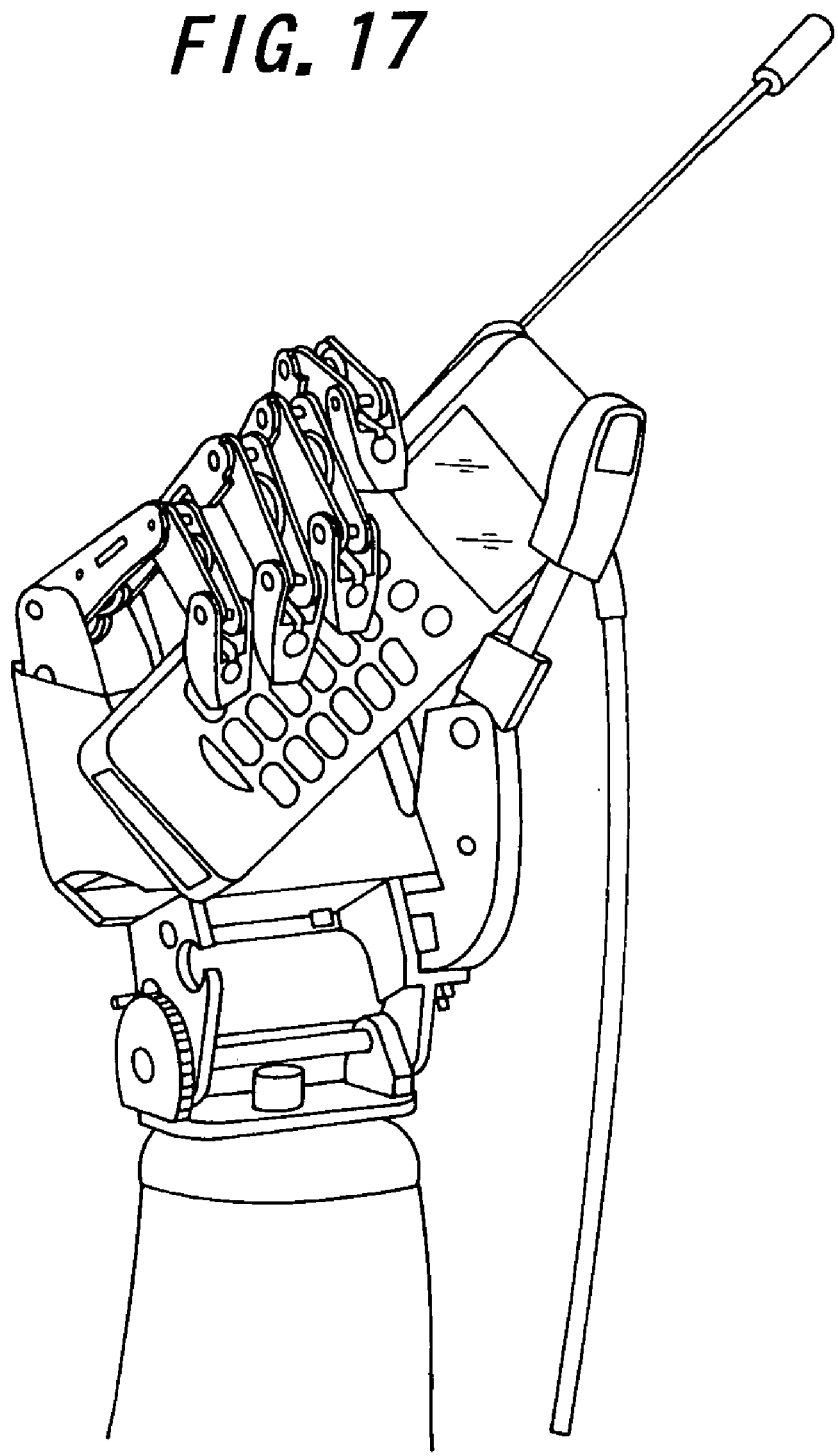
FIG. 17 is a perspective view showing an operation state of the upper extremity prosthesis of the applied example.

According to the upper extremity prosthesis of the applied example, by properly operating each movable finger from the thumb 41 to the little finger 45, it is possible to achieve various states, e.g., a hand-open state shown in FIG. 14, a state in smoking cigarette or the like shown in FIG. 15, a pen-holding state shown in FIG. 16, a portable telephone holding state shown in FIG. 17. In each of FIGS. 14 to 17, the bending mechanisms are also omitted.

Figure 18:
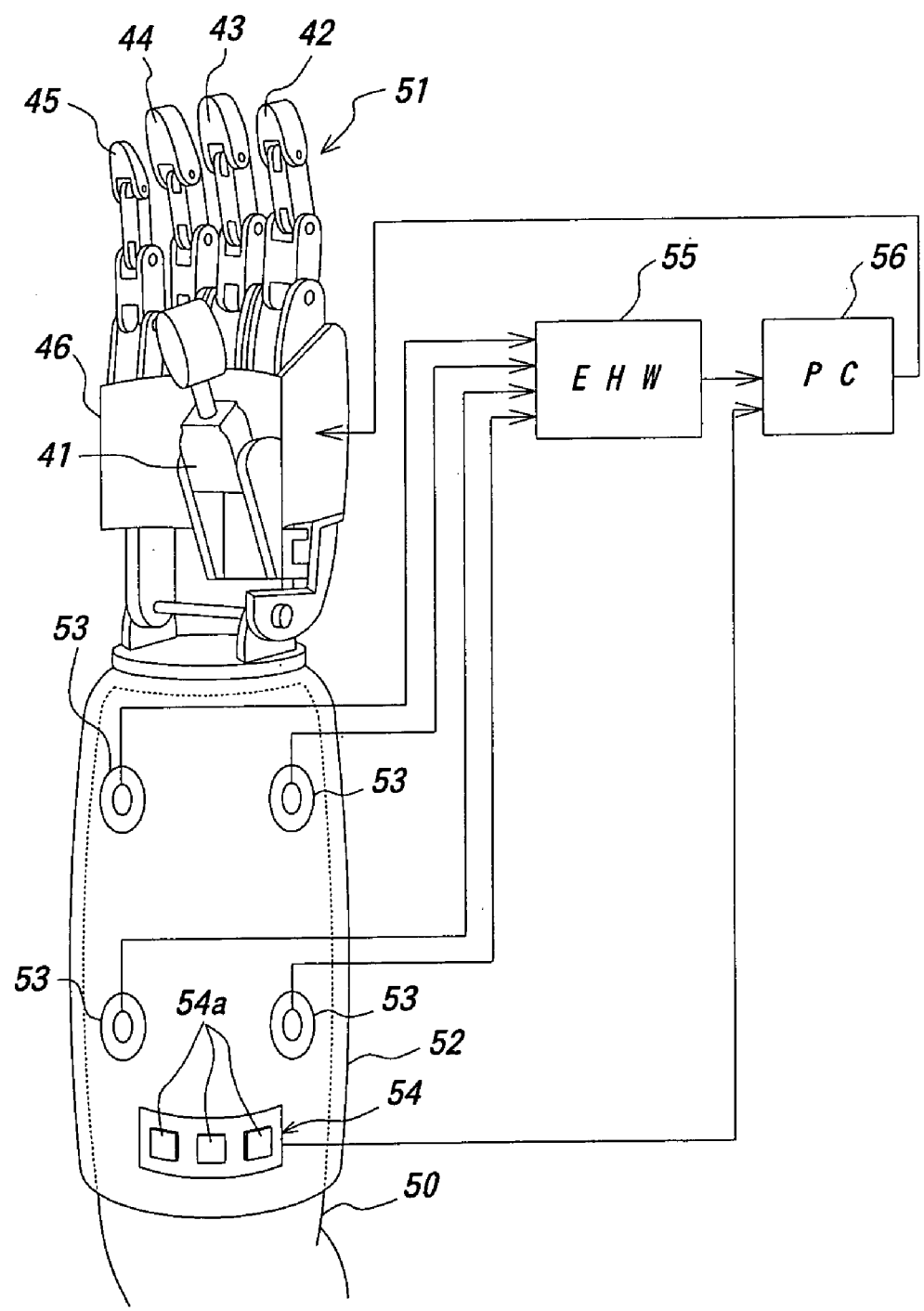
FIG. 18 is an explanation view illustrating a movable finger controller according to an embodiment of the invention.

FIG. 18 illustrates the constitution of a movable finger controller according to an embodiment of the invention, which is suitably used for integral control of the five movable fingers from the thumb 41 to the little finger 45 of the upper extremity prosthesis 51 of the foregoing applied example. As shown in the drawing, the controller of the embodiment includes: electrodes 53 as sensors provided in a plurality of places around a cylindrical holder 52, which is connected to the wrist of the upper extremity prosthesis 51 to put the upper extremity prosthesis 51 on a human arm 50 of no hand, so as to be brought into close contact with the skin of the arm 50 inserted into the holder 52, the electrodes 53 being adapted to detect a myoelectric signal flowing in the arm 50 by consciousness of the human with the arm 50 wearing the holder 52 to move a plurality of fingers; a touch type switch 54 as an operation mode changing means, having a plurality of touch panels 54a provided on the holder 52 to enable the human wearing the upper extremity prosthesis 51 to operate the plurality of touch panels 54a by the other hand or the like; known evolvable hardware (EHW) 55 including a programmable logic device (PLD) and a genetic algorithm in combination, which is adapted to receive myoelectric signals from the plurality of electrodes 53, learn a combination pattern of the myoelectric signals and output an operation command signal according to the combination pattern of the received myoelectric signals; and a normal programmable controller (PC) 56 including a microcomputer, which is adapted to receive a changing signal from the touch type switch 54 and the operation command signal from the EHW 55, output a driving signal to each servo motor for each of the five fingers from the thumb 41 to the little finger 45 of the upper extremity prosthesis 51 based on the received signals and a program pregiven according to the combination of these signals, and receive a rotational position signal from the rotary encoder in each servo motor to carry out a feedback-control of the operation of each movable finger of the upper extremity prosthesis 51.

For the EHW, one can be selected for use from, for example, a constitution provided by a thesis "ADAPTIVE HARDWARE DEVICES FOR REAL WORLD APPLICATIONS" described in Technical Report by The Institute of Electronics, Information and Communication Engineers, which describes the content of the invitation lecture of the workshop on real-time processing (RTP 1998) hosted by Computer System Research Group of Institute of Electronics, Information and Communication Engineers, and Executive Committee of the workshop on real-time processing, on Feb. 25, 1998, a constitution provided by a thesis "RESEARCH & DEVELOPMENT AND APPLICATIONS OF EVOLVABLE HARDWARE CHIPS" described in Proceedings of the 8th Fussy, Artificial Intelligence, Neutral Networks and Computational Intelligence Symposium held on 1998 (FAN 1998), and so on.

In the controller of the embodiment, when the electrodes 53 provided in the plurality of places of the human arm 50 wearing the upper extremity prosthesis 51 detect myoelectric signals flowing in the human arm 50 by the consciousness of moving the plurality of fingers caused by the human, and output the signals, the EHW 55 receives the myoelectric signals, learns the combination pattern of the myoelectric signals based on a genetic algorithm, and outputs an operation command signal according to the combination pattern. Then, the PC 56 receives the operation command signal from the EHW 55, and a changing signal from the touch type switch 54 operated by the human, and carries out the feedback-control of the operation of the respective servo motors of the five movable fingers of the upper extremity prosthesis 51 based on the received signals and a program pregiven according to the combination of these signals.

Thus, according to the controller of the embodiment, only by the consciousness of the human wearing the upper extremity prosthesis 51 to move the fingers, the five movable fingers of the upper extremity prosthesis 51 can be respectively operated. By making different the overall operational state of the five movable fingers depending on the combination pattern of the myoelectric signals from the plurality of electrodes 53, plural kinds of operations such as object gripping, hand opening, pointing, for example like those shown in FIGS. 14 to 17, can be carried out by the upper extremity prosthesis 51. In addition, the programmable logic device automatically changes the combination of logical circuits based on the genetic algorithm, and learns adaptability between the combination pattern of the myoelectric signals and the operational state of each movable finger in such a way as to receive an input of adaptability determination from the human wearing the upper extremity prosthesis 51, and output an operation command signal according to the combination pattern of the myoelectric signals outputted from the plurality of electrodes 53. Thus, the controller can learn the combination pattern of the signals within a very short time so as to cause the upper extremity prosthesis 51 to carry out a desired operation.

Furthermore, according to the controller of the embodiment, a program having a plurality of operation modes for one combination pattern can be beforehand provided to the PC 56. Thus, when the human wearing the upper extremity prosthesis 51 operates the touch switch 54 provided on the upper extremity prosthesis 51, an operation mode to be currently used can be changed among a plurality of operation modes, e.g., the operation mode of a plurality of fingers when a portable telephone set is held, the operation mode of a plurality of fingers when a pencil is held, and so on, with respect to e.g. a combination pattern for holding an object. Therefore, even if the number of combination patterns of myoelectric signals from the electrodes 53 is small, a complex operation suited to the use condition of the upper extremity prosthesis 51 can be carried out by the five movable fingers. Especially, the plurality of movable fingers can carry out time-sequential operations, such as sequential bending of fingers.

The invention has been described by way of illustrated examples. However, the invention is not limited to the foregoing examples. For example, the movable finger of the invention may be used for all, or two or three of the fingers of the upper extremity prosthesis. In addition, the movable finger of the invention can be used for a lower extremity prosthesis, if necessary. The first intermediate portion bending mechanism of the movable finger of the invention may be provided with a pulley having a winding portion of a constant distance from the first support shaft, instead of the eccentric member. Even in such a case, the foregoing operations and effects excluding the torque increase of the eccentric member can be provided. The actuator of the movable finger of the invention may be a hydraulic cylinder or a pneumatic cylinder operated by a pressure supplied from a pressure source such as an electric pump and an accumulator. Furthermore, some of the first to fifth thin string members of the movable finger of the invention may be thread-like substances made of, e.g., carbon fibers or the like, instead of metal wires, as long as they have limited elongation, but good flexibility and sufficient durability.

The sensor in the movable finger controller of the invention may be one directly adhered to the arm or the other part of the human wearing the prosthesis, and such a sensor may be adapted to detect a signal other than myoelectric one, e.g., the specific movement of the arm. In addition, the operation mode changing means may be one to change an operation mode not by the foregoing touch type switch but by a normal push type or a slide type switch, or a voice input.

Furthermore, the control of the movable finger of the invention may be carried out by omitting the foregoing sensor and the programmable logic device and entering an operation changing from the operation changing switch directly operated or operated by a voice input or the like to the normal programmable controller (PC). Alternatively, the bending operations and the straightening operations of the movable fingers may be carried out by being switched, separately by a plurality of changing switches corresponding to the plurality of movable fingers, or together by one switch of plural circuits and plural contacts that assemble the functions of the changing switches.

INDUSTRIAL APPLICABILITY

The present invention provides an upper extremity prosthesis capable of carrying out complex operations, and enables the upper extremity prosthesis to carry out complex operations easily.

What is claimed is:

1. A movable finger for at least one of a plurality of fingers of a prosthesis, comprising:
   a base disposed between a one of a back and a palm of a hand and between an instep and a sole of a foot;
   a first intermediate portion having a rear end swingably connected to a tip of the base through a first support shaft;
   a second intermediate portion having a rear end swingably connected to a tip of the first intermediate portion through a second support shaft; and
   a fingertip having a rear end swingably connected to a tip of the second intermediate portion through a third support shaft,
   wherein an actuator to pull one end of a first thin string member is disposed in the base, an eccentric member is disposed in a connected portion between said base and said first intermediate portion, the eccentric member being supported by said first support shaft so as to be rotated with respect to said base and said first intermediate portion and having a winding portion of an inconstant distance from the first support shaft, said first thin string member is passed through a finger inner side of said first support shaft and wound on said winding portion of said eccentric member, the other end of the first thin string member is connected to a portion of said eccentric member on a side, where said winding portion is separated from said first support shaft, the portion of said eccentric member is connected to a portion of said first intermediate portion which is closer to the tip of the first intermediate portion than said first support shaft through a first intermediate portion pulling spring, and a first intermediate portion straightening spring is inserted between said first intermediate portion and said base to always urge the first intermediate portion to take a straightened posture with respect to said base, thus constituting a first intermediate portion bending mechanism,
   a pulley wound with a second thin string member disposed in said first intermediate portion so as to be moved in a longitudinal direction thereof, one end of the second thin string member is connected to said base through a finger outer side of said first support shaft, the other end of the second thin string member is connected to the portion of said eccentric member on a side separated from the first support shaft, a third thin string member, one end of the third thin string member being connected to a support shaft of said pulley, the other end thereof connected through the finger inner side of said second support shaft to a portion of said second intermediate portion closer to the tip of the second intermediate portion than said second support shaft, and a second intermediate portion straightening spring is inserted between said second intermediate portion and said first intermediate portion to always urge said second intermediate portion to take a straightened posture with respect to said first intermediate portion, thus constituting a second intermediate portion bending mechanism, and a fourth thin string member, one end of the fourth thin string member being connected through a finger outer side of the second support shaft to a portion of said first intermediate portion closer to the rear end of the second intermediate portion than said second support shaft, the other end thereof connected through a finger inner side of said third support shaft to a portion of the fingertip closer to the tip of the second intermediate portion than the third support shaft, and a fifth thin string member, one end of the fifth thin string member being connected through a finger inner side of the second support shaft to the portion of said first intermediate portion closer to the rear end of the second intermediate portion than said second support shaft, the other end thereof connected through a finger outer side of the third support shaft to a portion of said fingertip closer to the tip of the second intermediate portion than the third support shaft, thus constituting a fingertip bending mechanism.

2. A movable finger for a prosthesis according to claim 1, wherein said other end of said second thin string member of the second intermediate portion bending mechanism is connected to said first intermediate portion instead of said eccentric member.

3. A movable finger for a prosthesis according to claim 2, wherein, in said fingertip bending mechanism, instead of or in addition to said fifth thin string member, a fingertip straightening spring is inserted between said fingertip and said second intermediate portion to always urge the fingertip to take a straightened posture with respect to said second intermediate portion.

4. A movable finger for a prosthesis according to claim 2, wherein said first intermediate portion bending mechanism includes, instead of said eccentric member, a pulley having a winding portion of a constant distance from said first support shaft.

5. An upper extremity prosthesis using a movable finger for a prosthesis specified in claim 2, comprising any one of a back and a palm of a hand;
wherein bases of the movable fingers for a prosthesis used for a plurality of fingers excluding a thumb are attached to said back or said palm of the hand in a curved arrangement to have a center of curvature in a palm side of the hand.

6. A movable finger for a prosthesis according to claim 1, wherein, in said fingertip bending mechanism, instead of or in addition to said fifth thin string member, a fingertip straightening spring is inserted between said fingertip and said second intermediate portion to always urge the fingertip to take a straightened posture with respect to said second intermediate portion.

7. A movable finger for a prosthesis according to claim 6, wherein said first intermediate portion bending mechanism includes, instead of said eccentric member, a pulley having a winding portion of a constant distance from said first support shaft.

8. An upper extremity prosthesis using a movable finger for a prosthesis specified in claim 6, comprising any one of a back and a palm of a hand;
wherein bases of the movable fingers for a prosthesis used for a plurality of fingers excluding a thumb are attached to said back or said palm of the hand in a curved arrangement to have a center of curvature in a palm side of the hand.

9. A movable finger for a prosthesis according to claim 1, wherein said first intermediate portion bending mechanism includes, instead of said eccentric member, a pulley having a winding portion of a constant distance from said first support shaft.

10. An upper extremity prosthesis using a movable finger for a prosthesis specified in claim 9, comprising any one of a back and a palm of a hand;
wherein bases of the movable fingers for a prosthesis used for a plurality of fingers excluding a thumb are attached to said back or said palm of the hand in a curved arrangement to have a center of curvature in a palm side of the hand.

11. An upper extremity prosthesis using a movable finger for a prosthesis specified in claim 1, comprising any one of a back and a palm of a hand;
wherein bases of the movable fingers for a prosthesis used for a plurality of fingers excluding a thumb are attached to said back or said palm of the hand in a curved arrangement to have a center of curvature in a palm side of the hand.

12. The upper extremity prosthesis according to claim 11, wherein said bases are attached to said back or said palm of the hand in said curved arrangement to be elastically swung.

* * * * *